United States Patent [19]

Kim et al.

[11] Patent Number: 5,554,603
[45] Date of Patent: Sep. 10, 1996

[54] ORALLY ACTIVE DERIVATIVES OF 1,3,5(10)-ESTRATRIENE

[75] Inventors: Hyun K. Kim, Bethesda; Richard P. Blye, Highland; Gabriel Bialy, Bethesda, all of Md.

[73] Assignee: The United States of America as represented by the Department of Health and Human Services, Washington, D.C.

[21] Appl. No.: 122,853

[22] Filed: Sep. 17, 1993

[51] Int. Cl.$^6$ .............................. A61K 31/56; C07J 1/00
[52] U.S. Cl. .......................... 514/182; 552/618; 552/626
[58] Field of Search .................................. 552/618, 626; 514/182

[56] References Cited

U.S. PATENT DOCUMENTS

| Re. 34,136 | 12/1992 | Crowe . |
| 3,980,681 | 9/1976 | Sykes . |
| 4,859,370 | 8/1989 | Crowe . |

FOREIGN PATENT DOCUMENTS

| 5.241 M | 7/1967 | France . |
| 1074493 | 7/1967 | United Kingdom . |
| 1145437 | 3/1969 | United Kingdom . |
| 1332784 | 10/1973 | United Kingdom . |

| WO87/00175 | 1/1987 | WIPO .............................. C07J 41/00 |

OTHER PUBLICATIONS

Sykes, P. J., et al. (1971) "Oxidation of Ring A–Aromatic Steroids To 9,11β–Diol 11–Nitrates Wtih Ceric Ammonium Nitrate", *Tetrahedron Letters*, 37:3393–3396.

Pellicciari, Roberto, et al. (1987) "An Efficient Procedure For The Regiospecific Preparation of D–Homo–Steroid Derivatives" *Steroids* 49:433–441.

Peters, Richard H., et al. (1989) "11β–Nitrate Estrane Analogues: Potent Estrogens" *J. Med. Chem.* 32:2306–2310.

Hasrat Ali, et al. (1993) "7α–Methyl– and 11β–Ethoxy–Substitution of [$^{125}$I]–16α–Iodoestradiol: Effect on Estrogen Receptor–Mediated Target Tissue Uptake" *J. Med. Chem.* 36:264–271.

Chemical Abstracts, vol. 83, No. 1, Jul. 7, 1975, Columbus, Ohio, USA, Abstract No. 1164g, I. Kun, "Estrogenic Action of Some New Nitrate Esters of Estradiol", p. 18, col. 2; see abstract & Rev.Med., vol. 20, No. 2, 1974, ROM pp. 190–193.

*Primary Examiner*—Kimberly J. Kestler
*Attorney, Agent, or Firm*—Townsend and Townsend and Crew

[57] ABSTRACT

The invention presents 17β-nitro and 11β, 17β-dinitro esters of estradiol which are made from 3-acyloxy-17-keto- or 3,17-dihydroxy-1,3,5-estratrienes by processes known in the art. The compounds exhibit estrogenic activity.

9 Claims, 4 Drawing Sheets

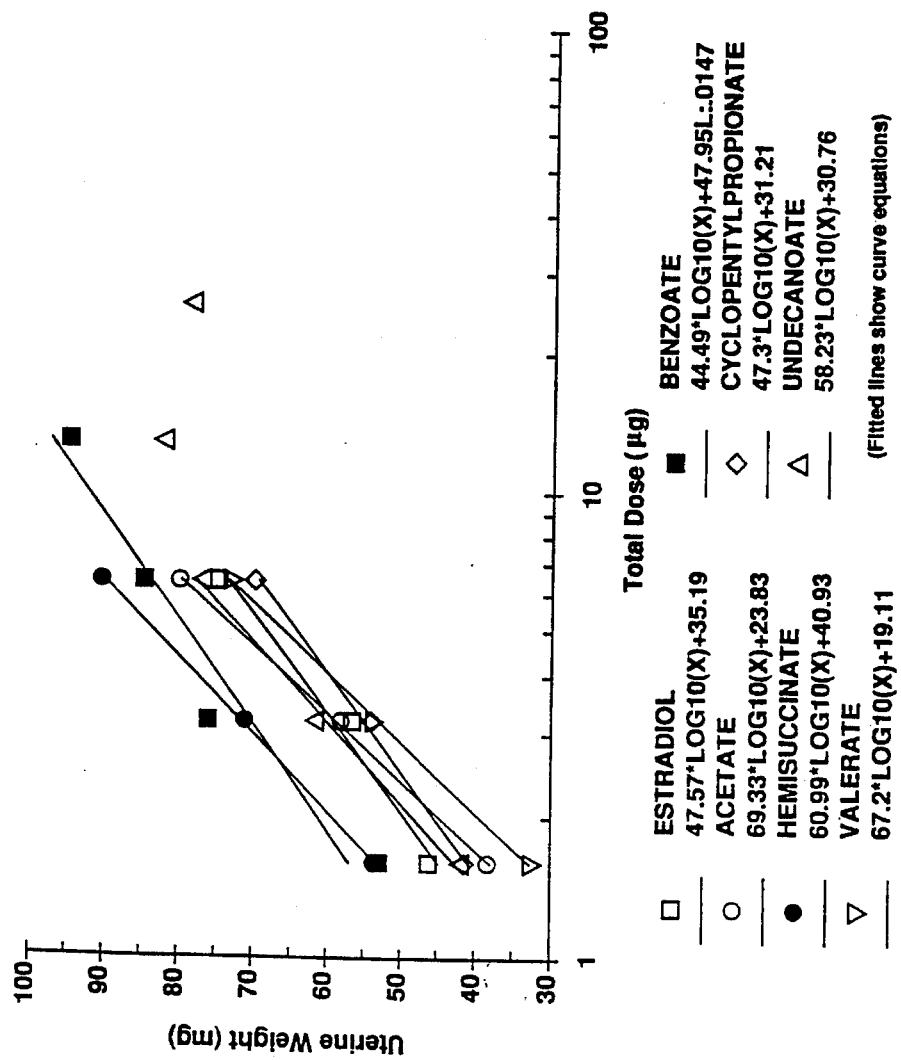
Fig. 1 ORAL ESTROGENIC ACTIVITY OF 17-ESTERS OF ESTRADIOL MEAN RAT UTERINE WEIGHTS (n=10) AND FITTED LINES

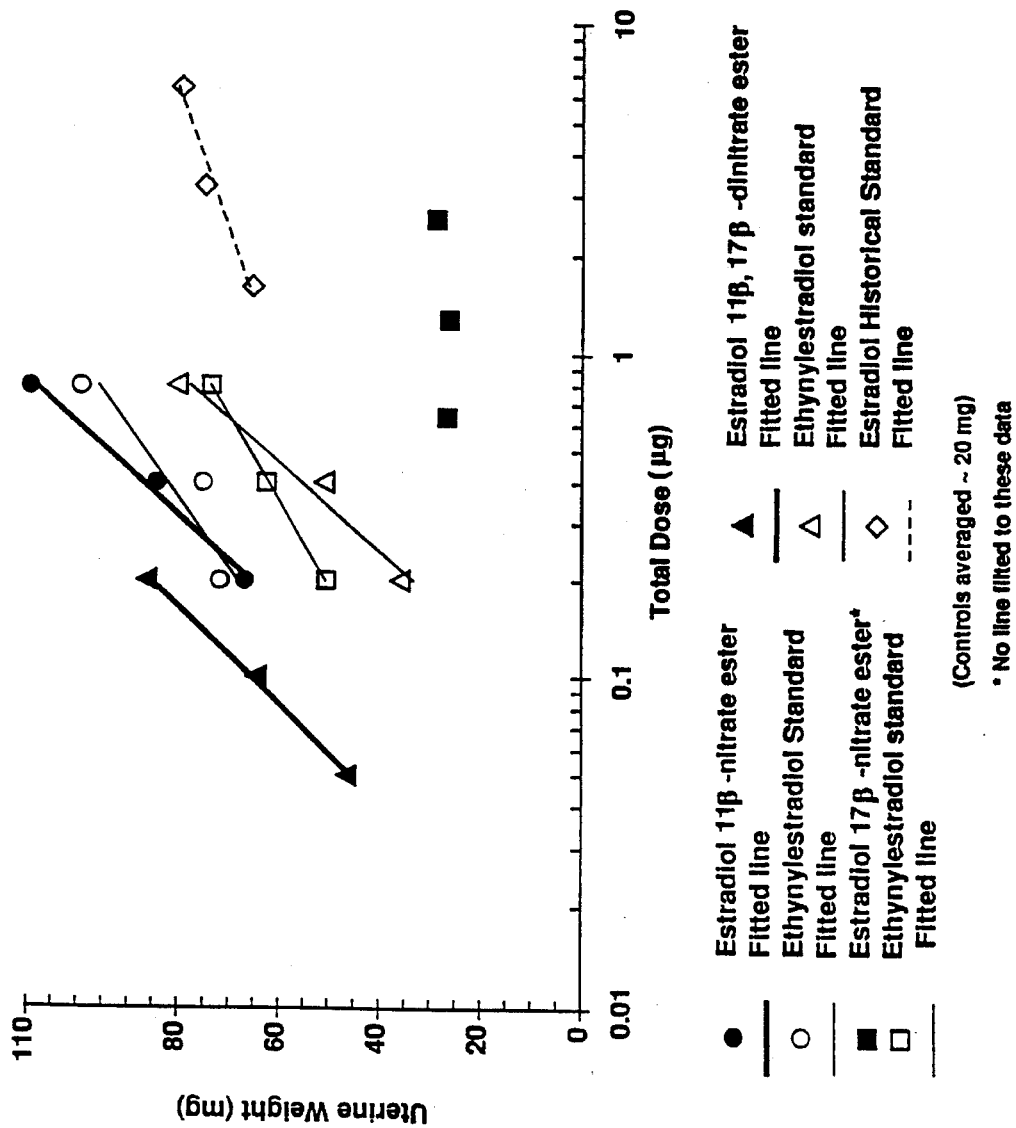
Fig. 2 ORAL ESTROGENIC ACTIVITY - RAT UTERINE WEIGHT METHOD

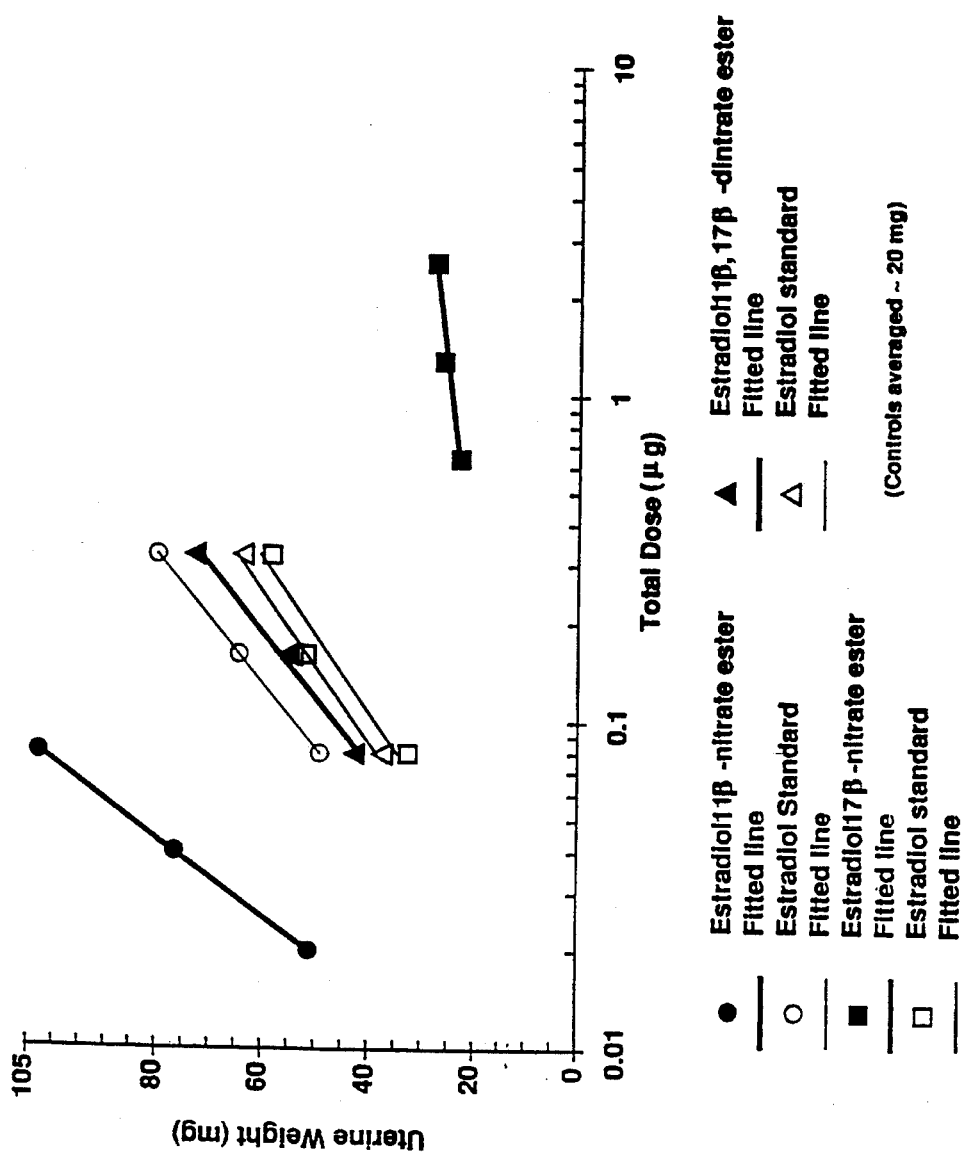
Fig. 3 SUBCUTANEOUS ESTROGENIC ACTIVITY - RAT UTERINE WEIGHT METHOD

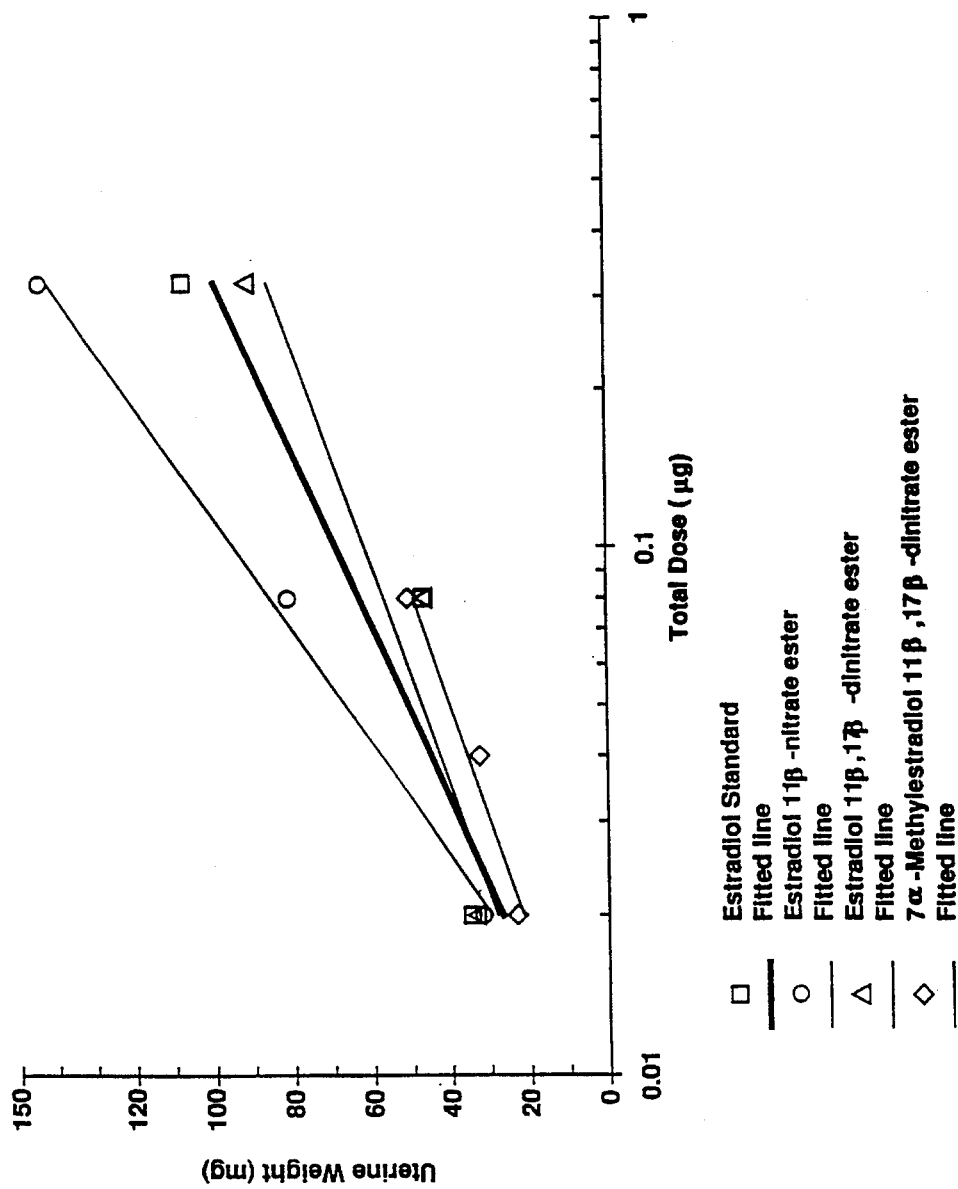

ORALLY ACTIVE DERIVATIVES OF 1,3,5(10)-ESTRATRIENE

BACKGROUND OF THE INVENTION

The present invention relates to esters of estradiol which exhibit potent oral and parenteral estrogenic activity. The invention provides pharmaceutical compositions comprising the compounds and methods for their use.

The utility of estrogenic substances in the practice of medicine is well documented. Estrogens may be used for the replacement of the natural hormone, estradiol, in hypogonadism and following removal of the ovaries or cessation of ovarian activity during menopause. They are also widely employed as a component of oral contraceptives. The natural hormones, estradiol and estrone are only weakly active upon oral administration and, therefore, relatively large dosages must be employed. The most frequently used oral preparations, 17α-ethynylestradiol and its 3-methyl ether, are synthetic derivatives of the natural hormone. Oral activity appears to be due to the presence of the 17-ethynyl group which protects the molecule from degradation by the liver following absorption from the gut and passage into the hepatoportal system (so-called "first pass effect").

While the advantages of estradiol and ethynylestradiol are substantial, as evidenced by their wide commercial adoption, these products are not without their drawbacks. These "ethynylated" estrogens have been associated with a number of side effects some of which are serious in nature (Smith, R. L., In: Briggs, M. H. and Diczfalusy, E. (Eds.): *Pharmaceutical Models in Contraceptive Development* Copenhagen, Bogtrykkeriet Forum, 1974). These problems are extremely serious when viewed in terms of the large number of women who take preparations such as those listed above on a long and regular basis. These problems include enhancing the risk of endometrial carcinoma; induction of malignant carcinoma especially in the cervix, breast, vagina and liver; promotion of gallbladder disease, thromboembolic and thrombotic diseases, myocardial infarction, hepatic adenoma, elevated blood pressure, and hypercalcemia; and a worsening of glucose tolerance. These problems tend to manifest themselves at the dosage levels needed to achieve the desired primary estrogenic and contraceptive effects. Many of these side effects are considered to be dose-related. If more potent oral estrogens were available, particularly those lacking the ethynyl group, they could be used in lower doses and the side effects could, at least in part, be reduced or eliminated.

Accordingly, it is desirable to have orally active estrogens lacking the ethynyl group which are clinically superior to those currently available. It is also desirable to have potent parenterally active estrogens in those circumstances where medical prudence favors administration by such routes. The present invention addresses these and other needs.

BACKGROUND ART

Esterification of naturally occurring estrogens is described in Emmens, C. W. and Martin L. Estrogens. In: Dorfman, R. I. (Ed.): *Methods in Hormone Research, Vol III, Part A* New York, Academic Press, 1964). More recently, Baldratti et al., *Experientia* 25:1018–1019 (1969) reported on the synthesis and estrogenic potency of a series of 3 and/or 17 modified analogs of 9α-hydroxyestrone 11-nitrate ester. Subsequently, Sykes et al. *Tetrahedron Letters* 37:3393–3396 (1971) reported on the synthesis and configuration of 9α,11β-diol and 9β,11β diol estrone 11-nitrate and their 3-acetates. U.S. Pat. No. 4,705,783 (reissued as R34,136) describes the synthesis and biological activity of 9β,11β-substituted and 11β-substituted estranes including several 7α-methyl analogs. The subject matter of this patent is also reported in Peters et al., *J. Med. Chem.* 32:2306–2310, (1989). Another related patent is U.S. Pat. No. 4,859,370.

SUMMARY OF THE INVENTION

The present invention provides a family of novel, active estrogens. The compounds of the invention may be employed wherever estrogenic medication is required. Such uses include but are not limited to replacement therapy following surgical removal of the ovaries or during the menopause, as the estrogenic component in oral contraceptives, and for the treatment of senile or atrophic vaginitis, functional uterine bleeding, failure of ovarian development, acne, hirsutism and osteoporosis.

The invention provides esters of estradiol in appropriate pharmaceutical formulations which possess enhanced estrogenic activity following oral or parenteral administration. The compounds are particularly suitable for use as the estrogenic component of combined oral contraceptives. Preferred compounds include 11β,17β-dinitrate esters of estradiol and estradiol-3-acetate and the corresponding 7α-methyl derivatives.

This invention also includes pharmaceutical compositions useful for producing estrogenic effects in female mammals which comprise an effective amount of the compounds of the invention in an admixture with a pharmaceutically suitable excipient for both oral and parenteral administration such as those well known in the art. It also includes methods of treating a female mammal with effective amounts of pharmaceutical compositions containing compounds to achieve estrogenic and contraceptive effects.

BRIEF DESCRIPTION OF THE DRAWINGS

FIG. 1. Oral estrogenic activity following administration to immature female rats.

FIG. 2. Oral estrogenic activity following administration to immature female rats.

FIG. 3. Subcutaneous estrogenic activity following administration to immature female rats.

FIG. 4. Percutaneous estrogenic activity following administration to immature female rats.

DESCRIPTION OF THE PREFERRED EMBODIMENT

In describing the location of groups and substituent on the estradiol rings, the following numbering system will be employed.

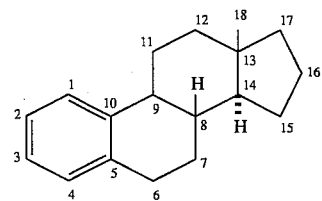

In these structures, the use of solid and dashed lines to denote particular conformation of groups follows the IUPAC steroid-naming convention.

The compounds of the invention can be used in combination with pharmaceutically acceptable carriers for all medical conditions for which estrogen use is indicated. Exemplary uses include use as the estrogenic component of combined oral contraceptives in female animals and wherever estrogenic activity is required to achieve a clinically acceptable means of contraception.

The present invention provides novel esters of estradiol such as compounds of the formula:

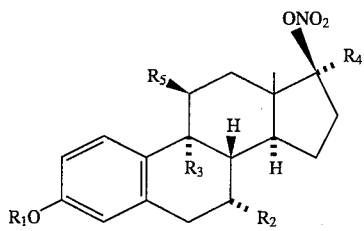

wherein $R_1$ is hydrogen, lower alkyl, cycloalkyl or lower acyl. Preferred substituents include acyl, in particular, acetyl groups.

$R_2$ is hydrogen or lower alkyl. Preferred substituents include hydrogen and methyl.

$R_3$ is hydrogen, hydroxy or lower alkoxy. Preferred substituents include hydrogen.

$R_4$ is hydrogen and lower alkyl. Preferred substituents include hydrogen.

$R_5$ is hydrogen and nitrate. Preferred substituents include nitrate.

As used herein, "alkyl" means a branched or unbranched saturated or unsaturated hydrocarbon group of one to twenty carbon atoms, including lower alkyls having one to eight carbons such as, methyl, ethyl, i-propyl and n-butyl and the like.

As used herein, "cycloalkyl" means a cyclic saturated hydrocarbon group of four to seven carbon atoms such as cyclobutyl, cyclopentyl, cyclohexyl and cycloheptyl and the like.

As used herein, "acyl" means an R—CO-group wherein R is an alkyl (typically lower alkyl). Exemplary acyls include $CH_3$—CO— (acetyl).

As used herein, "alkoxy" means an R—O-group wherein R is an alkyl, including lower alkyls. Alkoxies include methoxy, ethoxy and the like.

As a general class the compounds having the 11β, 17β-dinitrate esters are preferred. The compounds preferably possess a 9α, 11β- configuration and dextrorotary (+) optical activity. The preferred compounds of the invention include (+)-3,11β,17β-Trihydroxyestra-1,3,5(10)-triene 3-Acetate 11,17-Dinitrate Ester [Example 3], (+)-3,11β,17β-Trihydroxyestra-1,3,5(10)-triene 11,17-Dinitrate Ester [Example 4], (+)-3,11β,17β-Trihydroxy-7α-methylestra- 1,3,5(10)-triene 3-Acetate 11,17-Dinitrate Ester [Example 5], (+)-3, 11β,17β-Trihydroxy-7α-methylestra-1,3,5(10)-triene 11,17-Dinitrate Ester [Example 6], (+)-Estradiol 3-Acetate 17β-Nitrate Ester [Example 7] and (+)-7α-Methylestradiol 17β-Nitrate Ester [Example 8]. The preferred carriers are those pharmaceutical preparations commonly used for formulating tablets, capsules and other oral dosage forms well known in the art.

SYNTHESIS

Synthetic schemes for preparing the 11,17-dinitrate and 17-nitrate esters of estradiol are shown in Schemes 1–3, below. Detailed procedures for preparing particularly preferred species are given in Examples 1–8. Preparation of the $R_3$ and $R_5$ nitrate, halo, hydroxy and alkoxy substituted derivatives is also described in U.S. Pat. No. 4,859,370, and U.S. Pat. No. Re. 34,136, which are incorporated herein by reference.

Scheme 1
Synthesis of the 11-Nitrate Esters

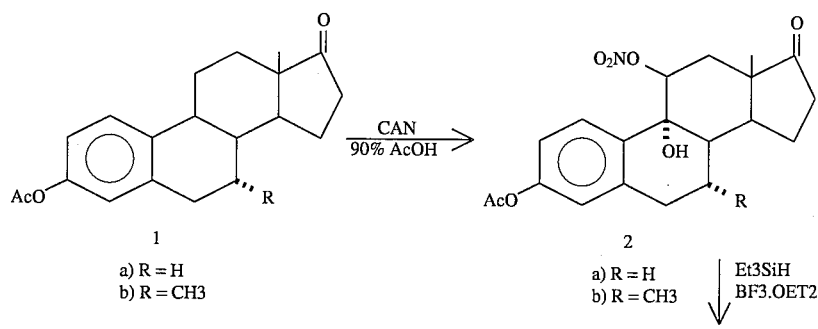

-continued
Scheme 1
Synthesis of the 11-Nitrate Esters
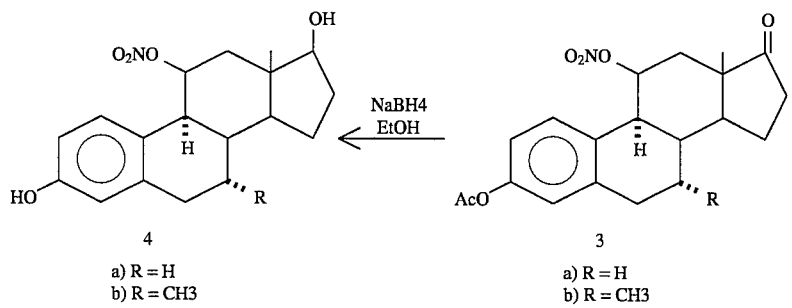
4
a) R = H
b) R = CH3
3
a) R = H
b) R = CH3
Scheme 2
Synthesis of the 11,17-Dintrate Esters
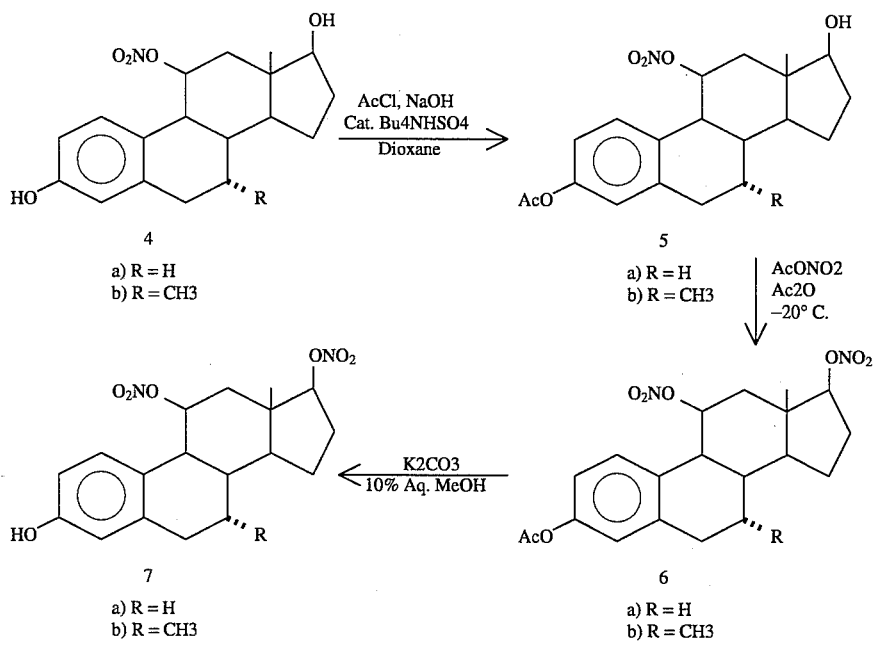
4
a) R = H
b) R = CH3
5
a) R = H
b) R = CH3
7
a) R = H
b) R = CH3
6
a) R = H
b) R = CH3
Scheme 3
Synthesis of the 17-Nitrate Esters
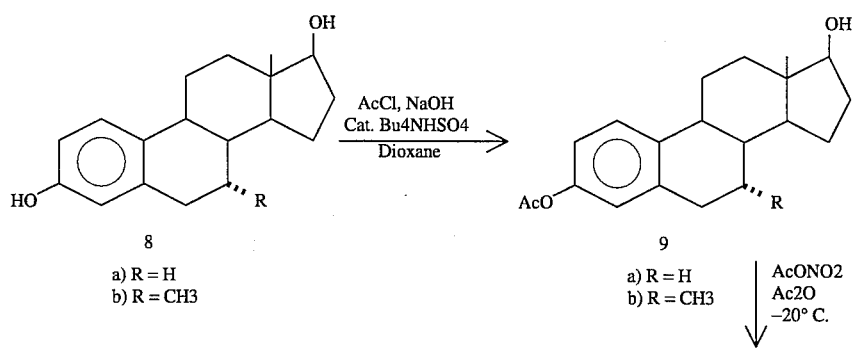
8
a) R = H
b) R = CH3
9
a) R = H
b) R = CH3

-continued
Scheme 3
Synthesis of the 17-Nitrate Esters

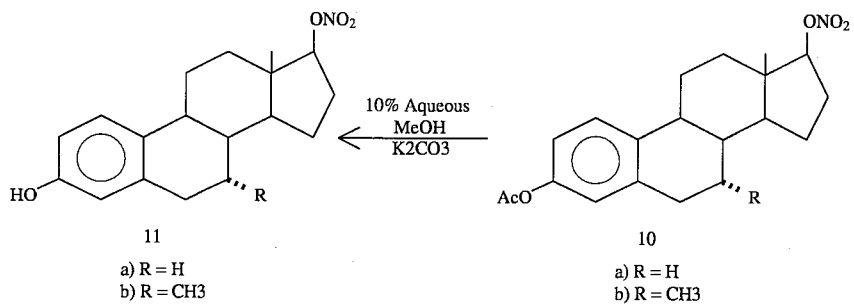

11
a) R = H
b) R = CH3

10
a) R = H
b) R = CH3

I. (+)-11β,17β-DINITRATE ESTERS OF ESTRADIOL AND ITS ANALOGS

Orally active (+)-estradiol 11β, 17β-dinitrate ester and its analogs were prepared from the corresponding (+)-11β-nitrate ester and its analogs. It was essential to acylate the 3-alcohol (4) selectively by means of phase transfer catalysis prior to nitration at C-17 as described by Baldratti et al., Experientia 25:1018–1019 (1969), which is incorporated herein by reference. Conversion of the phenolic OH at C-3 to the corresponding acetate stabilized the steroid molecule containing both 11β-nitrate and 11β,17β-dinitrate ester groups. In order to compare the biological activity of all of the nitrates, the (+)-17β-nitrate ester and its analogs were also prepared. These nitrate esters were synthesized as follows:

(A). 11β-NITRATE ESTERS OF ESTRADIOL AND ITS ANALOGS

Reaction of (+)-estrone acetate (1a), and (+)-7α-methylestrone acetate (1b) (preparation described in Peters et al., J. Med. Chem. 32:2306–2310 (1989) which is incorporated herein by reference), with ceric ammonium nitrate (CAN) in 90% acetic acid provided the predominant 9α-hydroxy 11β-nitrate isomers (2a,b) in 46, and 40% yield respectively. As reported in the literature (Sykes et al., Tetrahedron Lett. 37:3393–3396 (1971), which is incorporated herein by reference), a C-9 isomeric compound (11β-ONO₂, 9β-OH) was formed during the oxidation of (+)-estrone acetate (1a) with CAN in ~15–20% by TLC and NMR. The predominant 9α,11β-isomer was readily obtained after recrystallization or flash chromatography. Subsequent removal of the benzylic C-9 hydroxyl group using triethylsilane in the presence of $BF_3 \cdot Et_2O$ gave the predominant, 9α-H,11β-nitrate esters (3a,b) in ~50–63% yield, along with a 19:5 mixture of the undesired 9β-H,11β-ONO₂ and 9ε-H, 11β-ONO₂ and 17-εOH diastereomers shown by TLC, IR, and NMR. Reduction of the 17-ketone with sodium borohydride in ethanol followed by mild hydrolysis led to the desired nitrate esters (4a,b). Routine ¹H NMR examination of the 9-hydroxy 11-nitrate esters (2) confirmed the equatorial position of 11α-hydrogen, and the axial 9α-hydroxy orientation was assigned by analogy to prior chemical correlations made by Sykes et al., Peters et al., and Baldratti et al., supra.

When compound 4a was allowed to stand at room temperature without protection of light, this 11β-nitratoestradiol slowly decomposed to many unknown polar products as evidenced by reverse phase HPLC analysis, which could be attributed to the presence of free phenolic OH group. However, acetylation of the phenolic OH at C-3 rendered the stability to such asteroid molecule as compound 5a shown in Scheme 2.

(B). DINITRATE ESTERS OF ESTRADIOL AND ITS ANALOGS

Selective acylation of the 3-alcohol (4) in the presence of the 17-OH was required prior to subsequent nitration at C-17 and was conveniently accomplished under phase transfer catalytic conditions using acetyl chloride in anhydrous dioxane in the presence of powdered NaOH and catalytic amount of tetrabutylammonium hydrogen sulfate, as Illi, Tetrahedron Lett., 26:2431–2432 (1979), which is incorporated herein by reference. It gave the 3-acetate (5a) in 91% yield. Selective O-nitration of the 17-alcohol (5a) without concomitant nitration of the aromatic ring A at C-2 and C-4 was accomplished by using prior formation of acetyl nitrate and addition of this reagent to an acetic anhydride containing estradiol 3-acetate (9a). It gave exclusively the 17-nitrate ester in 76% yield. Indeed, treatment of 5a, as described above, afforded the 17-O-nitrate ester (6a) exclusively in 83% yield, without any trace amounts of aromatic ring-A nitrated products such as a mixture of 2-nitro- and 4-nitro 17-nitrate esters detectable by TLC and H NMR. Mild hydrolysis of 6a by $K_2CO_3$ provided the 11β,17β-dinitrate ester (7a) in nearly quantitative yield, as shown in Scheme 2. The dinitrate ester (7a) was purified by semi-preparative HPLC to a final purity of 99.2%. Their spectral data of ¹H NMR, IR and MS spectra are entirely consistent with the assigned structure. Unfortunately the dinitrate ester (7a) was found to be extremely unstable at room temperature. It began to decompose immediately after recrystallization. This instability of the dinitrate ester (7a) was overcome by acetylation of C-3 OH in a manner similar to that of the 11-nitrate ester (4a).

II. (+)-17β-NITRATE ESTERS OF ESTRADIOL AND ITS ANALOGS

Nitration of 9a,b using acetyl nitrate, as previously employed for the preparation of 6a,b afforded the 3-acetoxy-17-nitrate esters (10a,b) without any detectable amount of aromatic ring-A nitrated products as was evidenced by NMR and MS. Mild hydrolysis of 10a,b by $K_2CO_3$ in 10% aqueous MeOH proceeded smoothly to yield the desired compounds (11a,b) as shown in Scheme 3. In contrast to compounds 4a and 7a, the 17-nitrate esters show no decomposition at room temperature over the period of 6 months, when checked by HPLC.

The following examples will serve to disclose the synthesis of the compounds and the practice of the invention but are not to be considered limiting.

EXAMPLE 1

(+)-3,11β,17β-Trihydroxyestra-1,3,5(10)-triene 11-Nitrate Ester (4a)

Intermediate Preparation 1: (+)-3,9α, 11β-Trihydroxyestra- 1,3,5(10)-trien-17-one 3-Acetate 11-Nitrate Ester (2a). Following the procedure as described in Sykes, supra, treatment of (+)-estrone acetate (1a, 5.5 g, 17.6 mmol) (preparation described in Pellicciari et al., *Steroids* 49:433–441 (1987), which is incorporated herein by reference) in 90% acetic acid (115 mL), under nitrogen, and ceric ammonium nitrate (40.53 g, 73.9 mmol) gave 5.28 g of crude material, which consists of a 85:15 (or 80:20) mixture of 9α,11β- and 9β,11β-diol 11-nitrates shown by TLC and NMR. The solid was triturated with ether and finally recrystallized from acetone/hexanes to give 2.16 g of the predominant 9α,11β-diol 11-nitrate ester (2a), mp=179°–180° C. (lit. 183°–184° C.). Flash chromatography eluting with 3% acetone/$CH_2Cl_2$ Of the mother liquor gave an additional 0.8 g of material for an overall yield of 46% (3.16 g); IR(KBr) $v_{max}$ 3452, 1756, 1709, 1635, 1280 $cm^{-1}$; $^1$H NMR ($CDCl_3$) δ1.0 (3H, s, 18-$CH_3$), 2.25 (3H, s, 3-$OCOCH_3$), 5.83 (1H, t, J=3 Hz, 11α,-H), 6.80–7.05 (2H, m, C-2&C-4 H), 7.32 (1H, d, J=9 Hz, C-1 H).

Intermediate Preparation 2: (+)-3,11β-Dihydroxyestra-1,3,5(10)-trien-17-one 3-Acetate 11-Nitrate Ester (3a). Using the same procedure as described in Sykes et al., supra, the reaction of the 9α-alcohol (2a, 2.36 g, 6.06 mmol) in dry $CH_2Cl_2$ (100 mL) under a nitrogen atmosphere at ice-salt bath temperature, triethylsilane (3.4 mL, 21.2 mmol) and boronitrifluoride etherate (6.5 mL, 52.7 mmol) gave 2.3 g of a stable foam which consists of a 63:19:5 mixture of 9α-H, 11β-$ONO_2$, 9β-H, 11β-$ONO_2$, and 9ε-H, 11β-$ONO_2$, 17ε-OH diastereomers. Flash chromatography of the crude material eluting with 3% EtOAc/hexane gave 1.2 g (53%) of 3a, the predominant 9α-H, 11β-$ONO_2$ isomer; mp=187°–189° C. (lit. 190°–192° C.); IR (KBr) $v_{max}$ 2957, 1765, 1744, 1637, 1274 $cm^{-1}$; $^1$H NMR ($CDCl_3$) δ1.05 (3H, s, 18-$CH_3$), 2.25 (3H, s, 3-$OCOCH_3$), 6.10 (1H, q, J=3 Hz, 11α-H), 6.87 (m, C-2&C-4 H), 7.15 (d, J=9 Hz, C-1 H).

The Desired Product: (+)-3,11β,17β-Trihydroxyestra-1,3,5(10)-triene 11-Nitrate Ester (4a). The 3-acetoxy-17-ketone 11β-nitrate ester (3a, 0.537 g, 1.61 mmol) dissolved in 20 mL of abs. ethanol and THF (1:1) was treated with sodium borohydride (0.244 g, 6.44 mmol) and stirred for 3 hr under nitrogen. Acetic acid was added drop-wise until bubbling stopped. The mixture was diluted with ice-water and the pH was adjusted to 2–3 with aqueous HCl. The aqueous mixture was extracted with EtOAc (3x). The EtOAc layers were combined, washed with $H_2O$, and brine, and dried over anhydrous $Na_2SO_4$. Evaporation of the solvent gave 610 mg of the crude alcohol. Recrystallization of the crude material from acetone/hexanes afforded 0.43 g (84%) of 4a as a white, fluffy solid; mp=146°–148° C.; $[α]_D^{25}$=+60.8°(C=0.72, dioxane); IR(KBr): $v_{max}$ 3581, 3347, 2981, 1703, 1279 $cm^{-1}$; $^1$H NMR ($d_6$-acetone) δ0.90 (3H, s, 18-$CH_3$), 2.42 (1H, d of d, J=15 Hz, J'=3 Hz, 9α-H), 3.75 (1H, m, 17α-H), 6.10 (1H, q, J=3 Hz, 11α-H), 6.65 (2H, m, C-2&C-4 H), 7.05 (1H, d, J=9 Hz, C-1 H). MS(EI) m/z (rel intensity) 333 ($M^+$, 35), 270 ($M^+$—$HNO_3$, 100). Anal Calcd for $C_{18}H_{23}NO_3 \cdot CH_3OH$; C, 62.43; H, 7.45; N, 3.83. Found: C, 62.61; H, 7.41; N, 3.59.

EXAMPLE 2

(+)-3,11β,17β-Trihydroxyestra-1,3,5(10)-triene 3-Acetate 11-Nitrate Ester (5a). Powdered NaOH (180 mg, 4.5 mmol), and tetrabutylammonium hydrogen sulfate (6 mg, 0.02 mmol) were added to a well stirred solution of 11β-nitrate ester (4a, 600 mg, 1.8 mmol) in dry dioxane (8.0 mL). Acetyl chloride (1.0M) in dioxane (2.4 mL) solution was added slowly to the above mixture. During the course of the addition, the mixture became increasingly turbid and the yellow color of the phenolate anion was quenched near the end of the addition. The mixture was allowed to settle out and the supernatant was transferred with a syringe to a tube and the solid was centrifuged out. The supernatant was transferred to a round bottom flask. All the solids were rinsed with additional dioxane and centrifuged. The combined dioxane supernatants were evaporated in vacuo to give 695 mg of an amorphous white foam, which failed to crystallize. Flash chromatography eluting with 5% acetone and $CH_2Cl_2$ afforded 585 mg(87%) of 5a. HPLC analysis on a NovaPak C18 column eluting with 50% aq. $CH_3CN$ at a flow rate of 1.0 mL/min and at 276 nm UV detector showed the material to be 100% pure, $t_R$=5.08 min. $[α]_D^{25}$=+57.0° (c=0.82, dioxane). FTIR (KBr, diffuse reflectance): $v_{max}$ 3405, 2949, 1757, 1619, 1498, 1211 $cm^{-1}$; $^1$H NMR($CDCl_3$) δ0.93 (3H, s, 18-CH3), 2.27(3H, s, 3-$OCOCH_3$), 2.47 (1H, d of d, J=15 Hz, J'=3 Hz, 9α-H), 3.75 (1H, br.m, 17α-H), 6.02 (1H, q, J=3 Hz, 11α-H), 6.78–7.00 (2H, m, C-2 & C-4 H), 7.12 (1H, d, J=9 Hz, C-1 H). MS(EI) m/z (rel intensity) 375 ($M^+$,20), 333 ($M^+$-(Ac-1), 100), 312 ($M^+$—$HNO_3$, 7), 269 ($M^+$-(Ac+$HNO_3$), 5). Anal. calcd for $C_{20}H_{25}NO_6$ C,63.98; H,6.44; N,3.73. Found: C,62.36; H,6.59; N,3.67 Ash, 1.1%.

EXAMPLE 3

(+)-3,11β,17β-Trihydroxyestra-1,3,5(10)-triene 3-Acetate 11,17-Dinitrate Ester (6a). Purified fuming $HNO_3$ (55 μL, 1.37 mmol, prepared by treating red fuming nitric acid with solid urea while purging with air until the acid was colorless) was added to cold acetic anhydride (6.0 mL) at 0° C. under nitrogen. This mixture was stirred for 30 min and then added drop-wise to a cold (−20° C.), well stirred acetic anhydride (6.0 mL) solution of 5a (293 mg, 0.78 mmol). The reaction mixture was stirred at −20° C. for 1.25 hr and then poured into ice-water. The aqueous mixture was extracted with EtOAc (3x). The EtOAc layers were combined, washed with saturated $NaHCO_3$ (3x), $H_2O$ (1x), and brine, and dried over $Na_2SO_4$. Evaporation of the solvent gave 300 mg of a white powder. Recrystallization of the crude material from acetone/hexane gave 269.4 mg (86%) of 6a as colorless crystals in two crops; mp=160°–161° C. Analysis by HPLC on a NovaPak C18 eluting with 35% aq $CH_3CN$ at a flow rate of 1.0 mL/min, and at 276 nm uv detector showed 6a to be 100% pure, $t_R$=5.58 min; $[α]_D^{25}$=+35.62° (c=0.73, dioxane) ; IR(KBr): $v_{max}$ 2936, 1764, 1631, 1616, 1274, 1205 $cm^{-1}$; $^1$H NMR (CDCl3) δ 1.0 (3H, s, 18-CH3), 2.25 (3H, s, 3-OCOCH3), 2.50 (1H, d of d, J=15 Hz, J=3 Hz, 9α-H), 5.95 (1H, t, J=6 Hz, 17α-H) , 6.01 (1H, q, J=3 Hz, 11α-H), 6.90 (2H, m, C-2 & C-4 H), 7.15 (1H, d, J=9 Hz, C-1 H); MS (EI) m/z (rel intensity), 420 ($M^+$, 10), 378 ($M^+$-(AC-1),60), 358 ($M^+$-$NO_3$,10), 146 (100). Anal. Calcd for $C_{20}H_{24}N_2O_8$ C,57.14; H,5.75; N, 6.66. Found: C,57.13; H,5.72; N, 6.58.

EXAMPLE 4

(+)-3,11β,17β-Trihydroxyestra-1,3,5(10)-triene 11,17-Dinitrate Ester (7a). To a solution of 6a (294 mg, 0.70 mmol) in 10% aq methanol (50 mL) and enough THF (~10 mL), 10% aq potassium carbonate slowly was added, and the mixture was stirred for 2 hr. The solids were removed by filtration and the filtrate was evaporated. The residue was taken up into H₂O and the pH was adjusted to 2–3 with aqueous HCl. The aq mixture was extracted with EtOAc (3x). The EtOAc layers were combined, washed with H₂O and brine, and dried over $Na_2SO_4$. Evaporation of the solvent gave 280 mg of 7a as a stable foam, which was purified via semi-preparative HPLC (3 runs) on a Magnum ODS-3 10μ column eluting with 30% aq $CH_3CN$ at a flow rate of 9 mL/min to afford a yellow foam of 99.2% pure 7a; 201.3 mg (76% yield); IR(KBr) $v_{max}$ 3550, 3312, 2924, 1623, 1279 cm$^{-1}$; $^1$H NMR (CDCl₃) δ 1·00 (3H, s, 18-CH₃), 2.50 (1H, d of d, J=15 Hz, J'=3 Hz, 9α-H), 4.90 (1H, t, J=6 Hz, 17α-H), 5.95 (1H, q, J=3 Hz, 11α-H), 6.62 (2H, m, C-2&C-4 H), 6.95 (1H, d, J=9 Hz, C-1 H). MS (EI) m/z (rel intensity) 378(M⁺, 25), 315 (M⁺—HNO₃, 15), 286 (20), 146 (100).

EXAMPLE 5

[+]-3,11β,17β-Trihydroxy-7α-methylestra-1,3,5(10)-triene 3-Acetate 11,17-Dinitrate Ester (6b).

Intermediate Preparation 1: (+)-3,9α,11β-Trihydroxy-7α-methylestra-1,3,5(10)-trien-17-one 3-Acetate 11-Nitrate Ester (2b). Following the procedure described in Peters et al., supra, 2b was obtained in 12.25 g (40% yield) from (+)-7α-methylestrone acetate (25.67 g, 78.64 mmol), and ceric ammonium nitrate (176.6 g, 0.32 mol) in 90% acetic acid (505 mL); mp=177°–180° C. dec (lit. 184°–186° C.); IR(KBr) $v_{max}$ 3500, 2760, 1730, 1632, 1208 cm$^{-1}$; $^1$H NMR (CDCl₃) δ 1.00 (3H, s, 18-CH₃), 1.07 (3H, d, 7α-CH₃), 2.27 (3H, s, 3-OCOCH₃), 5.70 (1H, t, J=3 Hz, 11α-H), 6.95 (1H, s, C-4 H), 7.00 (1H, m, C-2 H), 7.40 (1H, d, J=9 Hz, C-1 H).

Intermediate Preparation 2: (+)-3,11β-Dihydroxy-7α-methylestra-1,3,5(10)-trien-17-one 3-Acetate 11-Nitrate Ester (3b). Using the same procedure as described in Peters et al., supra, the reaction of the 9α-alcohol (2b, 25.75 g, 63.83 mmol) in dry $CH_2Cl_2$ (990 mL) under a nitrogen atmosphere at ice-salt bath temperature, triethylsilane (35.2 mL, 219.48 mmol) and borontrifluoride etherate (68.2 mL, 552.94 mmol) gave 11.62 g (47% yield) of pure deoxygenated product 3b upon recrystallization from $CH_2Cl_2$-ether; mp=189°–191° C. dec (lit. 195°–196° C.); IR(KBr) $v_{max}$ 1770, 1748, 1637, 1204 cm$^{-1}$; $^1$H NMR (CDCl₃) δ 0.88 (3H, d, J=7 Hz, 7α-CH₃), 1.07 (3H, s, 18-CH,), 2.27 (3H, s, 3-OCOCH₃), 6.12 (1H, m, 11α-H), 7.05 (3H, br.m., aromatic H).

Intermediate Preparation 3: (+)-3,11β,17β-Trihydroxy-7α-methylestra-1,3,5(10)-triene 11-Nitrate Ester (4b). Following the procedure of Peters et al., supra, reduction of 3b (14.80 g, 42.60 mmol) in 720 mL of THF-EtOH (1:1) with NaBH₄ (7.10 g, 189.68 mmol) in 144 mL of EtOH-H₂O (1:1) gave 15.69 g of the crude product as a foam. Recrystallization of the crude foam from $CH_2Cl_2$ gave 10.05 g (68%) of the pure 4b as white plates; mp=179°–180° C. dec (lit 179°–182° C.); $[\alpha]_D^{27}$=+41.94° (c=0.76, dioxane); IR(KBr) $v_{max}$ 3375, 1675 cm$^{-1}$; $^1$H NMR (CDC₃:CD₃OD, 1:1) δ 0.83 (3H, d, J=7 Hz, 7α-CH₃), 0.90 (3H, s, C-18 CH₃),3.75 (1H, m, C-17α-H), 6.07 (1H, m, 11α-H), 6.60 (1H, s, C-4 H), 6.65 (1H, m, C-2 H), 7.03 (d, J=8 Hz, C-1 H); MS(EI) m/z (rel intensity) 347 (M⁺,9.0), 284 (M⁺-HNO₃,100), 251 (20), 225 (19).

Intermediate Preparation 4: (+)-3,11β,17β-Trihydroxy-7α-methylestra-1,3,5(10)-triene 3-Acetate 11-Nitrate Ester (5b). Powdered NaOH (144.09 mg, 3.6 mmol), and tetrabutylammonium hydrogen sulfate (5.0 mg, 1 mol %) were added to a solution of 4b (500 mg, 1.44 mmol) in dioxane. With vigorous mixing, acetylchloride (1.9 mL, 1.0M) in dioxane was slowly added to the above mixture. During the course of the addition, the mixture became increasingly turbid and the initial yellow color began to fade. The reaction mixture was centrifuged and the clear supernatant was transferred to a round bottom flask. The solids were leached with dioxane and re-centrifuged. The combined dioxane supernatants were evaporated in vacuo to afford 623 mg of 5b. Flash chromatography of this foam eluting with 4% acetone/$CH_2Cl_2$) gave 547 mg (97%) of 5b as a stable foam. IR(KBr): $v_{max}$ 3590, 2960, 1752, 1614, 1207, 1190 cm$^{-1}$; $^1$H NMR (CDCl₃) δ 0.83 (3H, d, J=6 Hz, 7α-CH₃), 0.93 (3H, s, 18-CH₃), 2.23 (3H, s, OCOCH₃), 2.4 (1H, d of d, J=15 Hz, J'=3 Hz, 9α-H), 3.72 (1H, br.t, J=6 Hz, 17α-H), 6.00 (1H, q, J=3 Hz, 11α-H), 6.72–6.92 (2H, m, C-2&C-4 H,), 7.15(1H, d, J=9 Hz, C-1 H). MS (EI) m/z (rel intensity), 389 (M⁺), 347 (M⁺-(Ac-1)), 283, 147 (100).

The Desired Product: (+)-3,11β,17β-Trihydroxy- 7α-methylestra-1,3,5(10)-triene 3-Acetate 11,17-Dinitrate Ester (6b). Purified fuming nitric acid (107 μL, 2.37 mmol) was added to cold acetic anhydride (2.0 mL) at 0° C. and the solution was stirred at 0° C. for 15 minutes. The above solution was added slowly with a syringe to a solution of 5b (526 mg, 1.35 mmol) in acetic anhydride (8 mL) at –20° C. The reaction mixture was stirred at –20° C. for additional 1.5 h. The reaction mixture was poured into ice-water. The mixture was extracted with EtOAc. The EtOAc extracts were combined, washed with saturated NaHCO₃ solution (3x), H₂O and brine, and dried over $Na_2SO_4$. Evaporation of the solvent gave 582 mg of a white solid. Recrystallization of this solid from acetone/hexane gave 429.5 mg (73%) of 6b mp=186°–187° C.; FTIR(KBr): $v_{max}$ 2903, 1762, 1616, 1211 cm$^{-1}$; $^1$H NMR (CDCl₃) δ 0.83 (3H, d, J=6 Hz), 1.00 (3H, s, 18-CH₃), 2.23 (3H, s, 3-OCOCH₃), 2.40 (1H, d of d, J=15 Hz, J'=3 Hz, 9α-H), 4.93 (1H, t, J=6 Hz, 17α-H), 6.03 (1H, q, J=3 Hz, 11α-H), 6.72–6.92 (2H, m, C-2&C-4 H); MS(EI) m/z(rel intensity) 434 (M⁺), 392 (M⁺-(Ac-H)), 300, 160 (100).

EXAMPLE 6

(+)-3,11β,17β-Trihydroxy-7α-methylestra- 1,3,5(10)-triene 11,17-Dinitrate Ester (7b). An aqueous NaOH solution (0.5N, 1.8 mL, 0.91 mmol) was added to a methanol suspension of the 3-acetate (6b, 316 mg, 0.73 mmol). Within 15 minutes the mixture became homogeneous and no starting material was shown by TLC. The reaction mixture was made acidic with HCl to pH=3–4 and the methanol was evaporated. The residue was suspended in H₂O and the aq mixture was extracted with EtOAc. The EtOAc extracts were combined, washed with H₂O and brine, and dried over $Na_2SO_4$. Evaporation of the solvent gave 311 mg of a solid. Recrystallization of this solid from acetone/hexanes gave 219 mg (76%) of a white solid, mp=172°–173° C. dec. Recrystallization of the mother liquor gave an additional 65 mg (23%). $[\alpha]_D^{27}$=+21.99 (C=0.68, dioxane): Anal. Calcd. for $C_{19}H_{24}N_2O_7$, C,58.15; H,6.17; N,7.14. Found: C,57.77; H,6.06; N,6.83

EXAMPLE 7

(+)-Estradiol 17β-Nitrate Ester (11a):

Intermediate Preparation 1: Estradiol 3-Acetate (10a). Acetyl chloride (6.2 mL of 1.0M in dioxane) was added drop-wise over 45 min to a stirred mixture of (+)-estradiol (8a, 1 g, 3.67 mmol), powdered NaOH (0.367 g, 9.18 mmol), and tetrabutylammonium hydrogen sulfate (12 mg, 3.5 mmol %) in dry dioxane (20 mL). After the addition was complete, the reaction mixture was filtered through a sintered glass funnel with Celite, and the solvent was evaporated. The residue was taken up into $CHCl_3$ and washed with $H_2O$ (1x) and brine (1x). The $CHCl_3$ layer was dried over anhydrous $Na_2SO_4$, filtered and evaporated to yield 1.19 g of foam. The material was purified by flash chromatography eluting with acetone:$CH_2Cl_2$(5:95) to yield 920 mg (92% yield) of the 3-acetate (9a); mp=138°–139° C.; IR(KBr) $v_{max}$ 3492, 3053, 2922, 1736, 1464, 1372, 1242 $cm^{-1}$; 1H NMR ($CDCl_3$) δ 0.90 (3H, s, 18-CH3), 2.25 (3H, s, 3-OAc), 3.75 (1H, t, J=6 Hz, 17α-H), 6.85–7.30 (3H, m, C-1,C-2,&C-4 H).

Intermediate Preparation 2: (+)-Estradiol 3-Acetate 17β-Nitrate Ester (10a). Purified fuming nitric acid (204.5 μL, 4.45 mmol) was added to cold acetic anhydride (10 mL) at 0° C. under nitrogen. The mixture was stirred for 15 min and then added drop-wise to a cold (−20° C.), stirred acetic anhydride (10 ml) solution of 9a (800 mg, 2.54 mmol). The reaction mixture was stirred at −20° C. for 1 h and then poured into ice-water. The aqueous mixture was extracted with EtOAc (3x). The EtOAc layers were combined, washed with saturated $NaHCO_3$ (3x), $H_2O$ (1x), and brine, and dried over $Na_2SO_4$. Evaporation of the solvent yielded 0.96 g of crude product. It was dried overnight to remove residual acetic anhydride, giving 900 mg (99% yield) of 10a. Without further purification it was used for the subsequent step; mp=102°–103° C.; $^1$H NMR ($CDCl_3$) δ 0.9 (3H, s, 3H, C-18 $CH_3$), 2.27 (3H, s, 3-$OCOCH_3$), 4.93 (1H, t, J=6 Hz, 17α-H), 6.85–7.30 (3H, m, C-1,C-2&C-4 H).

The Desired Product: (+)-Estradiol 17β-Nitrate Ester (11a). To dissolve a suspension of 10a (820 mg, 2.28 mmol) in 10% aq MeOH (100 ml), was added enough THF (25 mL). The reaction mixture was treated with $K_2CO_3$ (0.5 g, 3.62 mmol) and stirred 2 hr. The solids were removed by filtration and the filtrate was evaporated. The residue was taken up into $H_2O$ and extracted with EtOAc (3x). The EtOAc layers were combined, washed with $H_2O$ and brine, and dried over anhydrous $Na_2SO_4$. Evaporation of the solvent yielded 725 mg of crude product 11a. Recrystallization of the crude material from acetone:hexanes, gave 480 mg (54% yield); mp=182°–183° C.; HPLC analysis on a Waters' NovaPak $C_{18}$ column using 35% aq $CH_3CN$ as an eluent at a flow rate of 1 mL/min with $\lambda_{max}$=280 indicated it to be 98% pure. $[\alpha]_D^{25}$=+71.00 (C=1.01, 95% EtOH); IR(KBr) $v_{max}$ 3553, 2932, 1610, 1501, 1441, 1272 $cm^{-1}$; $^1$H NMR ($CDCl_3$) 0.9 (3H, s, 18-$CH_3$), 4.93 (1H, t, 17-H), 6.57 (3H, m, aromatic); MS (EI) m/z (rel intensity) 317 ($M^+$,70), 253 (11), 159 (100). Anal. Calcd for $C_{18}H_{23}NO_4$; C,68.10; H,7.31; N,4.42. Found: C,68.30; H,7.32; N,4.42.

EXAMPLE 8

(+)-7α-Methylestradiol 17β-Nitrate Ester (11b):

Intermediate Preparation 1: (+)-7α-Methylestradiol 3-Acetate (9b). Powdered NaOH (150 mg, 3.75 mmol), and tetrabutylammonium hydrogen sulfate (5 mg, 0.02 mmol) were added to a well stirred solution of (+)-7α-methylestradiol (8b, 430 mg, 1.5 mmol) in dioxane. Preparation of (+)-7α-methylestradiol is described in Kalvoda et al., *Helv. Chim. Acta* 50:281–288 (1967), which is incorporated herein by reference. Acetyl chloride (1.0M) (1.95 mL, 1.95 mmol) in dioxane was added slowly to the above mixture. During the course of addition, the reaction mixture became increasingly turbid and the initial yellow color was quenched near the end of the addition. The reaction mixture was centrifuged and the dioxane supernatant was transferred to a round bottom flask. The solids were leached with additional dioxane and centrifuged (2x). The combined dioxane supernatants were evaporated in vacuo to afford 470 mg of a stable foam. Flash chromatography eluting with 3% acetone/$CH_2Cl_2$ gave 400 mg (81%) of 9b as a stable foam; FTIR (KBr, diffuse reflectance): $v_{max}$ 3475, 2879, 1753, 1200 $cm^{-1}$; 1H NMR ($CDCl_3$) δ 0.73 (3H, s, 18-CH3), 0.80 (3H, d, J=6 Hz, 7α-CH3), 2.23 (3H, s, 3-$OCOCH_3$), 3.10 (1H, d of d, J=15 Hz, J'=6 Hz, 7β-H), 3.73 (1H, t, J=6 Hz, 17α-H), 6.70–6.95(2H, m, C-2&C-4 H), 7.30 (1H, d, J=9 Hz,C-1 H); MS (EI) (rel intensity) 328 ($M^+$), 286 ($M^+$-(Ac-1), 100).

Intermediate Preparation 2: (+)-7α-Methylestradiol 3-Acetate 17β-Nitrate Ester (10b). Purified fuming nitric acid (51 μL, 1.28 mmol) was added to acetic anhydride (2.0 mL) at 0° C. and the solution was stirred for 15 min more at 0° C. The above acetyl nitrate solution was added slowly with a syringe to a solution of 9b (239 mg, 0.73 mmol) at −20° C. The reaction mixture was stirred at −20° C. for 1.5 h. The reaction mixture was poured into ice-water and the aqueous mixture was extracted with EtOAc. The EtOAc extracts were combined, washed with a saturated $NaHCO_3$ solution (3x), $H_2O$ (1x), and brine, and dried over $Na_2SO_4$. Evaporation of the solvent gave 277 mg of a foam. Flash chromatography of this material eluting with 1% acetone/$CH_2Cl_2$ gave 236.2 mg (87%) of 10b as a foam. FTIR (KBr, diffuse reflectance): $v_{max}$ 2932, 1767, 1622, 1279, 1207 $cm^{-1}$; $^1$H NMR ($CDCl_3$) δ 0.83 (3H, d, J=6 Hz, 7a-$CH_3$), 0.88 (3H, s, 18-$CH_3$), 2.27 (3H, s, 3-OCOCH3), 3.13 (1H, d of d, J=15 Hz, J'=6 Hz, 7β-H), 4.95(1H, t, J=6 Hz, 17α-H), 6.75–7.00 (2H, m, C-2&C-4 H), 7.33 (1H, d, J=9 Hz, C-1 H); Ms (EI) m/z (tel intensity) 373 ($M^+$), 331 ($M^+$-(Ac-1), 100).

The desired product: (+)-7α-Methylestradiol 17β-Nitrate Ester (11b). A solution of 10b (236 mg, 0.63 mmol) in THF/MeOH (1:1, 20 mL) was treated with ag NaOH (0.5 N) (1.6 mL, 0.79 mmol) and the mixture was stirred for 15 min. The reaction mixture was made acidic (pH=3.4) with HCl and THF/MeOH was evaporated in vacuo. The residue was diluted with $H_2O$ and the aqueous mixture was extracted with EtOAc. The EtOAc extracts were combined, washed with $H_2O$, brine, and dried over $Na_2SO_4$. Evaporation of the solvent gave 220 mg of a stable foam. Flash chromatography of this material eluting with 1% acetone/$CH_2Cl_2$) gave 208 mg (100%) of 11b as a stable amorphous foam. $[\alpha]_D^{25}$=+ 62.7° (C=0.89, dioxane); FTIR(KBr, diffuse reflectance): $v_{max}$ 3300, 2930, 1620, 1501, 1278 $cm^{-1}$; $^1$H NMR ($CDCl_3$) δ 0.83 (3H, d, J=6 Hz, 7α-$CH_3$), 0.88 (3H, s, 18-$CH_3$), 3.13 (1H, d of d, J=15 HZ, J'=6 HZ, 7β-H), 4.95 (1H, t, J=6 Hz, 17α-H), 6.50–6.78 (2H, m, C-2&C-4 H), 7.20 (1H, d, J=9 Hz, C-1 H); MS(EI) m/z (tel intensity): 331($M^+$, 90), 267 ($M^+$-($HNO^3$+H), 14), 173 (96), 159 (64), 147 (100). Anal. Calcd. for $C_{19}H_{25}NO_4$ C, 68.85; H, 7.61; N, 4.23. Found: C, 68.69; H, 7.47; N, 4.23.

BIOLOGICAL ACTIVITY

Methods

The estrogenic activity of the compounds of the invention can be tested in a variety of assays well known to those skilled in the art (see, e.g., Re. 34,136). As described below, the compounds were tested for estrogenic activity using the rat uterine weight method. Selected compounds were also studied for postcoital activity in rats and estrogen withdrawal bleeding in ovariectomized rhesus monkeys. Details of these studies and the results obtained therefrom are described below.

Estrogenic Activity—Rat Uterine Weight Method

Immature (approximately 21 day old) female rats of the Sprague-Dawley strain were maintained under standard conditions of housing and allowed free access to food and water. Light was controlled so that there were 12 hours of illumination and 12 hours of darkness in each 24 hour period. Test compounds were prepared by dissolving them in absolute ethanol and then adding enough sesame oil so that the final concentration of ethanol was 10%. Animals were randomized to groups of ten rats each and assigned to one of three dose levels of standard or test material or for the vehicle control. Test compounds were administered by gavage (orally), by subcutaneous injection or by direct application to the skin in an alcoholic solution daily for three consecutive days. Estradiol-17β was employed as the subcutaneous standard and ethynylestradiol was used as the oral standard. Both estradiol and ethynylestradiol were employed as standards for the transdermal route. Rats were sacrificed 24 hours after the last dose and the uteri excised, cleaned of fat and connective tissue, blotted on moist filter paper and weighed to the nearest 0.1 mg. Means and standard error of the means were calculated and the means plotted on semilog graphs. Curve fitting, potency ratios and conventional statistics were undertaken using the PROPHET data management system (Holford, N. "Drug model in Prophet Public Procedures" BBN System and Technologies, Cambridge, Mass., 1990).

Postcoital Activity—Adult Mated Rats

Adult female rats of the Sprague-Dawley stain were maintained under standard conditions of housing including free access to food and water and cycles of 12 hours of light and 12 hours of darkness. Following establishment of regular four-day estrous cycles, proven breeder males were placed overnight with females in proestrus. The following morning males were removed and vaginal smears obtained to verify the occurrence of mating by the presence of sperm. Females which showed evidence of mating were randomly assigned to dose groups for the test material, standard or control consisting of ten animals each. Test compounds and standards were dissolved in 10% ethanol/sesame oil and administered daily for five consecutive days starting on the day sperm were observed in the vaginal washings. Controls received vehicle only. Animals were sacrificed on day 10 of presumptive pregnancy and the number and condition of conceptuses recorded. Potency was expressed in terms of the $ED_{100}$.

Estrogen Withdrawal Bleeding—Ovariectomized Rhesus Monkeys

Ovariectomized rhesus monkeys maintained under accepted conditions of housing and welfare were randomly assigned to groups of approximately five animals each. Animals received the test material or standard in bread soaked with a sesame oil solution daily for ten consecutive days. Controls received vehicle only. Standard estrogens cause uterine bleeding upon cessation of treatment, usually within 14 days. The onset, duration and intensity of this withdrawal bleeding was used as a measure of estrogenic potency in this species.

RESULTS

Estrogenic Activity

Results of biological tests are summarized in Table 1. The 11-nitrato ester exhibited a 10-fold increase in the oral estrogenic activity and a 4 to 7-fold increase in the subcutaneous activity of estradiol. The 11,17 dinitrato ester showed a 56-fold increase in the oral estrogenic activity but only a slight increase in the subcutaneous activity of the free alcohol. Curiously, the 17-mononitrate ester was virtually devoid of estrogenic activity by either route. This was entirely unexpected since esterification at position 17 usually enhances activity or at least the duration of action following parenteral administration, but has little effect on, and certainly does not reduce, oral activity (FIG. 1). The finding that the oral activity of the 11, 17 dinitrato ester was substantially greater than that of the 11-nitrate ester was totally unanticipated in view of the foregoing. These obervations are shown graphically in FIGS. 2 and 3. Subcutaneously, the 11-nitrate ester exhibited about 5 times the activity of estradiol while the 11, 17-dinitrate ester showed about the same activity as the free alcohol by this route. The 17-mononitrate ester was also inactive by subcutaneous injection.

7α-methylation of the 11-mononitrato ester resulted in a further increase in oral estrogenic potency of more than 10-fold, while 7α-methylation of the 11, 17-dinitrate ester produced only a small increase in activity. In addition, 7α-methylation of the 17-mononitrate ester yielded a compound with modest oral activity somewhat less potent than estradiol itself. Following subcutaneous administration 7α-methylation produced a further increase of about 2-fold in estrogenic potency of both the 11-mono and 11,17-dinitrate esters of estradiol. Following 7α-methylation, the 17-mononitrate ester appeared about 10% as active as estradiol.

Acetylation at position 3 had only a modest effect on the oral and parenteral estrogenic activity of the 11-nitrato and 11, 17-dinitrato esters of estradiol.

Following percutaneous (transdermal) administration the 11-nitrato and the 11,17-dinitrato esters as well as their respective 7α-methyl analogs exhibited activity similar to that of estradiol (FIG. 4).

Postcoital Activity

The 11-nitrato and 11,17-dinitrato esters exhibited 5-fold and 100-fold increases respectively in the oral postcoital activity of estradiol in the rat. These results parallel the findings for enhanced estrogenic activity.

Estrogen Withdrawal Bleeding

The 11-nitrate and 11,17-dinitrate esters showed about the same potency as estradiol following oral administration to rhesus monkeys using uterine bleeding following withdrawal of hormonal support as the endpoint. This could be the result of poor oral absorption or rapid metabolism and excretion in this nonhuman primate species. It is also interesting to note that estradiol which is some 10 times less potent than 17α-ethynylestradiol in the rat oral uterotropic test is equally active in inducing withdrawal bleeding following oral administration to rhesus monkeys.

Based upon these experiments, compounds of the invention provide estrogenic activity equal to or greater than ethynylestradiol or its 3-methyl ether, following oral administration. These compounds also have utility when administered by parenteral routes and by intravenous injection or transdermal application.

The compounds of this invention can be administered to humans or other mammals by any of the accepted modes of administration for steroidal agents. These methods include oral, parenteral, suppositories, topical and the like. The compounds can be administered alone or as part of a combination product—such as with a progestin or the like.

Depending on the intended mode of administration, the compositions used may be in the form of solid, semi-solid or liquid dosage forms, such as, for example, injectables, suppositories, pills, capsules, powders, liquids, suspensions, or the like, preferably in unit dosage forms suitable for single administration of precise dosages. The compositions will include a conventional pharmaceutical carrier or excipient and an active compound of the invention and, in addition, may include other medicinal agents, pharmaceutical agents, carriers, adjuvants, etc. For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, sucrose, magnesium carbonate, and the like. Such compositions take the form of solutions, suspensions, tablets, pills, capsules, powders, sustained release formulations and the like.

The compounds of the invention as defined above may be formulated as suppositories using, for example, polyalkylene glycols, for example, propylene glycol, as the carrier.

Liquid pharmaceutically administrable compositions particularly for parenteral administration (generally characterized by injection—subcutaneously, intramuscularly or intravenously) can be prepared by dissolving, dispersing, etc. a compound of the invention and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see Remington's *Pharmaceutical Sciences*, Mack Publishing Company, Easton, Pa., 15th Edition, 1975. The composition or formulation to be administered will, in any event, contain a quantity of the active compound(s) adequate to achieve the desired estrogenic or contraceptive effect in the subject being treated.

The therapeutic compositions are administered to a patient already suffering from a disease, as described above, in an amount sufficient to cure or at least partially arrest the symptoms of the disease and its complications. Alternatively, the compounds can be used for replacement therapy following surgical removal of the ovaries or during the menopause, as the estrogenic component in oral contraceptives. An amount adequate to accomplish the desired effect is defined as an "effective dose." Amounts effective for this use will depend on the weight and general state of the patient and the judgement of the prescribing physician. Oral pills and tablets may contain from 0.01 mg to about 1.0 mg of active material, while a dose of injectable composition may comprise from about 0.01 mg to about 10 mg of the active material.

The invention has been described in the above examples and disclosure in some detail for the purposes of clarity and understanding. It will be apparent, however, that certain changes and modifications may be practiced within the scope of the appended claims.

TABLE 1

EFFECT OF MODIFICATION OF CERTAIN 1,3,5(10)-ESTRATRIENES ON BIOLOGICAL ACTIVITY

| CDB | Position | | | | | | Estrogenic Activity[a] | | | Postcoital** |
|---|---|---|---|---|---|---|---|---|---|---|
| No. | 3 | 7α | 9α | 11β | 17α | 17β | Oral, Rat | Subcu, Rat | EWB | Oral, Rat |
| 100 | OH | | | | | OH | 10 | 100 | 40 | 250 |
| 104 | OH | | | | C≡CH | OH | 100 | 714 | 32 | 200 |
| 3280 | OH | | | ONO$_2$ | | OH | 121 | 432–735 | 64 | ~50 |
| 3616 | OH | | | | | ONO$_2$ | Inactive | Inactive | | |
| 3535 | OH | | | ONO$_2$ | | ONO$_2$ | 560 | 130 | 32 | 2.5 |
| 1357 | OH | Me | | ONO$_2$ | | OH | 1441 | 760–1484 | 80 | 5 |
| 3677 | OH | Me | | | | ONO$_2$ | 5–10 | 7–10 | | |
| 3660 | OH | Me | | ONO$_2$ | | ONO$_2$ | 670 | 286 | | |
| 3700 | Ac | | | ONO$_2$ | | OH | 75 | 610–980 | | |
| 3701 | Ac | | | ONO$_2$ | | ONO$_2$ | 437 | 51 | | |

*Estrogenic Activity
Oral, Rat
Rat uterine weight method, CDB-104 (EE) = 100% (assigned)
Subcu, Rat
Rat uterine weight method, CDB-104 (E2) = 100% (assigned)
EWB
Oral ED$_{100}$ (μg/day × 10 days) for withdrawal bleeding in ovariectomized rhesus monkeys
**Postcoital Oral ED$_{100}$ (μg/day × 5 days) for postcoital activity in the rat

What is claimed is:

1. A compound of the formula

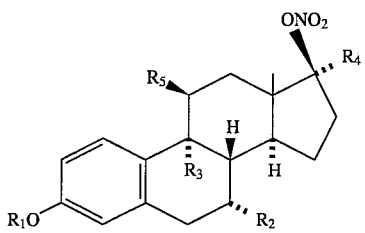

wherein $R_1$ is selected from the group consisting of hydrogen, lower alkyl, cycloalkyl and lower acyl;

$R_2$ is selected from the group consisting of hydrogen and lower alkyl;

$R_3$ is selected from the group consisting of hydrogen, hydroxy and lower alkoxy;

$R_4$ is selected from the group consisting of hydrogen and lower alkyl; and $R_5$ is nitrate.

2. The compound of claim 1 wherein $R_3$ and $R_4$ are hydrogen.

3. The compound of claim I wherein $R_1$ is H.

4. The compound of claim 1 wherein $R_1$ is acetyl.

5. The compound of claim 1 wherein $R_2$ is methyl.

6. The compound of claim 1, which is selected from the group consisting of (+)-3,11β,17β-Trihydroxyestra-1,3,5(10)-triene 3-Acetate 11,17-Dinitrate Ester, (+)-3,11β,17β-Trihydroxyestra-1,3,5(10)-triene 11,17-Dinitrate Ester, (+)-3,11β,17β-Trihydroxy-7α-methylestra-1,3,5(10)-triene 3-Acetate 11,17-Dinitrate Ester, and (+)-3,11β,17β-Trihydroxy-7α-methylestra-1,3,5(10)-triene 11,17-Dinitrate Ester.

7. A pharmaceutical composition useful for producing an estrogenic effect in a female mammal which comprises an effective amount of a compound of claim 1 in admixture with a pharmaceutically acceptable excipient.

8. The pharmaceutical composition of claim 7, wherein the compound is selected from the group consisting of (+)-3,11β,17β-Trihydroxyestra-1,3,5(10)-triene 3-Acetate 11,17-Dinitrate Ester, (+)-3,11β,17β-Trihydroxyestra-1,3,5(10)-triene 11,17-Dinitrate Ester, (+)-3,11β,17β-Trihydroxy-7α-methylestra-1,3,5(10)-triene 3-Acetate 11,17-Dinitrate Ester, and (+)-3,11β,17β-Trihydroxy-7α-methylestra-1,3,5(10)-triene 11,17-Dinitrate Ester.

9. A method of treating a female mammal to achieve an estrogenic effect which comprises administering to said mammal an effective amount of the pharmaceutical composition of claim 7.

* * * * *